(12) United States Patent
Kushida et al.

(10) Patent No.: US 10,259,817 B2
(45) Date of Patent: Apr. 16, 2019

(54) CRYSTAL (6S,9AS)-N-BENZYL-8-({6-[3-(4-ETHYLPIPERAZIN-1-YL)AZETIDIN-1-YL]PYRIDIN-2-YL}METHYL)-6-(2-FLUORO-4-HYDROXYBENZYL)-4,7-DIOXO-2-(PROP-2-EN-1-YL)HEXAHYDRO-2H-PYRAZINO[2,1-C][1,2,4]TRIAZINE-1(6H)-CARBOXAMIDE

(71) Applicant: Eisai R&D Management Co., Ltd., Tokyo (JP)

(72) Inventors: Ikuo Kushida, Tsukuba (JP); Yoko Ito, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 15/577,858

(22) PCT Filed: Jun. 21, 2016

(86) PCT No.: PCT/JP2016/068381
§ 371 (c)(1),
(2) Date: Nov. 29, 2017

(87) PCT Pub. No.: WO2016/208576
PCT Pub. Date: Dec. 29, 2016

(65) Prior Publication Data
US 2018/0141950 A1 May 24, 2018

Related U.S. Application Data

(60) Provisional application No. 62/183,577, filed on Jun. 23, 2015.

(51) Int. Cl.
C07D 487/04 (2006.01)
A61K 31/53 (2006.01)
A61P 35/00 (2006.01)

(52) U.S. Cl.
CPC ............ C07D 487/04 (2013.01); A61K 31/53 (2013.01); A61P 35/00 (2018.01); *C07B 2200/13* (2013.01)

(58) Field of Classification Search
CPC .................................................. C07D 487/04
See application file for complete search history.

(56) References Cited

U.S. PATENT DOCUMENTS

| 6,262,046 | B1 | 7/2001 | Alker et al. |
| 8,080,657 | B2 | 12/2011 | Chung et al. |
| 2010/0286094 | A1 | 11/2010 | Chung et al. |
| 2013/0196972 | A1 | 8/2013 | Chung et al. |
| 2015/0175615 | A1 | 6/2015 | Inoue et al. |

FOREIGN PATENT DOCUMENTS

| CL | 201102116 | 3/2009 |
| CL | 200003576 | 10/2009 |
| CL | 201402511 | 4/2012 |
| CL | 201502363 | 2/2013 |
| CL | 201601367 | 2/2013 |
| CN | 1585770 | 2/2005 |
| CN | 101827849 | 9/2010 |
| CN | 101896485 | 11/2010 |
| CN | 102046628 | 5/2011 |
| CN | 103209982 | 7/2013 |
| EP | 3 088 401 | 11/2016 |
| JP | 2011-500666 | 1/2011 |
| JP | 2011-522037 | 7/2011 |
| JP | 2013-540774 | 11/2013 |
| RU | 2457210 | 7/2012 |
| RU | 2470024 | 12/2012 |
| WO | WO 2001/046196 | 6/2001 |
| WO | WO 2006/123517 | 11/2006 |
| WO | WO 2009/051397 | 4/2009 |
| WO | WO 2009/148192 | 12/2009 |
| WO | WO 2010/101849 | 9/2010 |
| WO | WO 2010/120112 | 10/2010 |
| WO | WO 2012/115286 | 8/2012 |
| WO | WO 2013/151708 | 10/2013 |
| WO | WO 2014/130869 | 8/2014 |
| WO | WO 2015/098853 | 2/2015 |
| WO | WO 2015/098855 | 7/2015 |

OTHER PUBLICATIONS

International Preliminary Report on Patentability in International Patent Application No. PCT/JP2016/068381, dated Jan. 4, 2018, 9 pages (English Translation).

Barker and Clevers, "Mining the Wnt pathway for cancer therapeutics," Nature Reviews Drug Discovery, Dec. 2006, vol. 5, p. 997-1014.

Chen et al., "Small molecule-mediated disruption of Wnt-dependent signaling in tissue regeneration and cancer," Nature Chemical Biology, Feb. 2009, vol. 5 No. 2, p. 100-107.

(Continued)

*Primary Examiner* — Bruck Kifle
(74) *Attorney, Agent, or Firm* — Fish & Richardson P.C.

(57) ABSTRACT

The present invention provides a crystal of (6S,9aS)-N-benzyl-8-({6-[3-4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide.

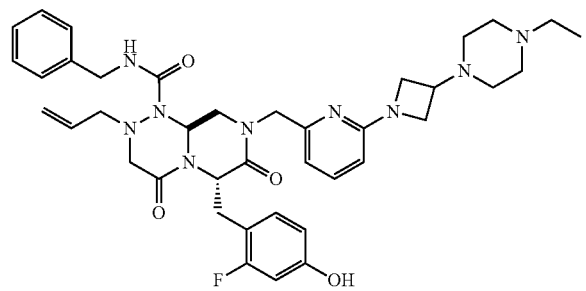

8 Claims, 6 Drawing Sheets
Specification includes a Sequence Listing.

(56) References Cited

OTHER PUBLICATIONS

De Robertis et al., "Identification and Characterization of a Small-Molecule Inhibitor of Wnt Signaling in Glioblastoma Cells," Mol Cancer Ther, Jul. 2013, vol. 12 No. 7, p. 1180-1189.
Emami et al., "A small molecule inhibitor of β-catenin/CREB-binding protein transcription," PNAS, Nov. 23, 2004, vol. 101 No. 4, p. 12682-12687.
Gurney et al., "Wnt pathway inhibition via the targeting of Frizzled receptors results in decreased growth and tumorigenicity of human tumors," PNAS, Jul. 17, 2012, vol. 109 No. 29, p. 11717-11722.
Hao et al., "Targeted Inhibition of β-Catenin/CBP Signaling Ameliorates Renal Interstitial Fibrosis,"J Am Soc Nephrol, 2011, vol. 22, p. 1642-1653.
Henderson, Jr. et al., "Inhibition of Wnt/β-catenin/CREB binding protein (CBP) signaling reverses pulmonary fibrosis", PNAS, Aug. 10, 2010, vol. 32, p. 14309-14314.
Huang et al., "Tankyrase inhibition stabilizes axin and antagonizes Wnt signaling," Nature, Oct. 2009, vol. 461, p. 614-620.
International Preliminary Report on Patentability in International Patent Application No. PCT/JP2014/0883932, dated Jul. 7, 2016, 5 pages.
International Search Report in International Patent Application No. PCT/JP2016/068381, dated Sep. 6, 2016, 2 pages (English Translation).
Jiang et al., "Inactivating mutations of RNF43 confer Wnt dependency in pancreatic ductal adenocarcinoma," PNAS, Jul. 30, 2013, vol. 110 No. 31, p. 12649-12654.
Lam et al., "β-catenin signaling: a novel mediator of fibrosis and potential therapeutic target," Curr Opin Rheumatol, Nov. 2011, vol. 23 No. 6, p. 562-567.
Lehtiö et al., "Tankyrases as drug targets," FEBS Journal, 2013, vol. 280, p. 3576-3593.
Notice of Allowance in U.S. Appl. No. 14/577,660, dated Jul. 9, 2015, 10 pages.
Search Report in European Patent Application No. 14873998.0, dated May 29, 2017, 6 pages.
Shitashige et al., "Traf2- and Nck-Interacting Kinase Is Essential for Wnt Signaling and Colorectal Cancer Growth," Cancer Res, Jun. 15, 2010, vol. 70 No. 12, p. 5024-5033.
Waaler et al., "Novel Synthetic Antagonists of Canonical Wnt Signaling Inhibit Colorectal Cancer Cell Growth," Cancer Research, Jan. 1, 2011, vol. 71 No. 1, p. 197-205.
Yao et al., "AV-65, a novel Wnt/β-catenin signal inhibitor, successfully suppresses progression of multiple myeloma in a mouse model," Blood Cancer Journal, 2011, vol. 1 e. 43, p. 1-9.
Notice of Allowance in Pakistan Patent Application No. 907/2014, dated May 2, 2018, 1 page (English Translation).
Notice of Allowance in Ukraine Patent Application No. a201606261, dated Feb. 22, 2018, 18 pages (English Translation).
Office Action in Australia Patent Application No. 2014371148, dated Mar. 28, 2018, 2 pages.
Office Action in Chile Patent Application No. 201601419, dated Feb. 13, 2018, 18 pages (English Translation).
Office Action in Gulf Cooperation Council Patent Application No. GC2014-28624, dated Jan. 7, 2018, 7 pages (English Translation).
Office Action in Vietnam Patent Application No. 1-2016-02104, dated Apr. 26, 2018, 4 pages (English Translation).
Official Notification in Gulf Cooperation Council Patent Application No. GC2014-28624, dated Apr. 5, 2018, 298 pages (English Translation).
Submission Document in Pakistan Patent Application No. 907/2014, dated Nov. 23, 2016, 6 pages (English Translation).
International Search Report in International Patent Application No. PCT/JP2014/083932, dated Mar. 17, 2015, 5 pages.
Notice of Allowance in Australian Patent Application No. 2014371148, dated Jul. 26, 2018, 4 pages (English Translation).
Notice of Allowance in Chinese Patent Application No. 201480067017.7, dated Sep. 13, 2018, 4 pages (English Translation).
Notice of Allowance in Gulf Cooperation Council Patent Application No. GC2014-28624, dated May 9, 2018, 2 pages (English Translation).
Notice of Allowance in Israeli Patent Application No. 245961, dated Jul. 26, 2018, 15 pages (English Translation).
Notice of Allowance in Japanese Patent Application No. P2015-554886, dated Jan. 24, 2017, 6 pages, (English Translation).
Notice of Allowance in Japanese Patent Application No. P2016-572771, dated Apr. 4, 2017, 6 pages (English Translation).
Notice of Allowance in Russian Patent Application No. 2016122867, dated Aug. 31, 2018, 30 pages (English Translation).
Notice of Allowance in Singaporean Patent Application No. 11201604496Y, dated Nov. 23, 2016, 5 pages.
Notice of Allowance in South African Patent Application No. 2016/03956, dated Nov. 2, 2017, 2 pages.
Office Action in Chinese Patent Application No. 201480067017.7, dated Mar. 1, 2017, 11 pages (English Translation).
Office Action in Colombian Patent Application No. 16147681, dated Jun. 27, 2017, 16 pages (English Translation).
Office Action in Israeli Patent Application No. 245961, dated Jul. 20, 2016, 5 pages (English Translation).
Office Action in Japanese Patent Application No. P2016-572771, dated Feb. 7, 2017, 6 pages (English Translation).
Office Action in Pakistani Patent Application No. 907/2014, dated Aug. 11, 2016, 2 pages.
Office Action in Russian Patent Application No. 2016122867, dated Jun. 18, 2018, 13 pages (English Translation).
Office Action in Taiwanese Patent Application No. 103144928, dated Jun. 7, 2018, 7 pages (English Translation).
Submission Document in Australian Patent Application No. 2014371148, date Jul. 10, 2018, 8 pages.
Submission Document in Chilean Patent Application No. 201601419, dated Jul. 13, 2018, 30 pages (English Translation).
Submission Document in Chinese Patent Application No. 201480067017.7, dated Jun. 5, 2017, 7 pages, (English Translation).
Submission Document in Colombian Patent Application No. 16147681, date Oct. 30, 2017, 39 pages (English Translation).
Submission Document in European Patent Application No. 14873998.0, dated Dec. 13, 2017, 11 pages.
Submission Document in Russian Patent Application No. 2016122867, dated Aug. 31, 2018, 8 pages.
Submission Document in Vietnamese Patent Application No. 1-2016-02104, dated Jun. 5, 2018, 18 pages (English Translation).
Notice of Allowance in European Patent Application No. 14873998.0, dated Oct. 17, 2018, 141 pages.
Notice of Allowance in Vietnamese Patent Application No. 1-2016-02104, dated Aug. 27, 2018, 2 pages (English Translation).
Official Notification in Chilean Patent Application No. 201601419, dated Sep. 21, 2018, 17 pages (English Translation).
Submission Document in Malaysian Patent Application No. PI2016702025, dated Oct. 4, 2018, 2 pages.
Submission Document in Taiwanese Patent Application No. 103144928, dated Sep. 5, 2018, 32 pages (English Translation).
Search Report in European Patent Application No. 16814346.9, dated Nov. 15, 2018, 8 pages.
Office Action in Taiwanese Patent Application No. 103144928, dated Nov. 13, 2018, 6 pages (English Translation).
Chen et al., "Solid-state nuclear magnetic resonance and its application in research of drug polymorphs," Chinese Journal of New Drugs, 2013, 22(16): 1921-1924, 1955 (with English Translation).
Office Action in Chinese Patent Application No. 201680030060.5, dated Jan. 30, 2019, 15 pages (with English Translation).
Submission Document in European Patent Application No. 16814346.9, dated Feb. 22, 2019, 9 pages.
Zhao et al., "Basics for the design and development of new drugs," Shandong University Press, 2015, p. 93-p. 94 (with English Translation).

CRYSTAL (6S,9AS)-N-BENZYL-8-({6-[3-(4-ETHYLPIPERAZIN-1-YL)AZETIDIN-1-YL]PYRIDIN-2-YL}METHYL)-6-(2-FLUORO-4-HYDROXYBENZYL)-4,7-DIOXO-2-(PROP-2-EN-1-YL)HEXAHYDRO-2H-PYRAZINO[2,1-C][1,2,4]TRIAZINE-1(6H)-CARBOXAMIDE

TECHNICAL FIELD

The present invention relates to a crystal of (6S,9aS)-N-benzyl-6-[(4-hydroxyphenyl)methyl]-4,7-dioxo-8-({6-[3-(piperazin-1-yl)azetidin-1-yl]pyridin-2-yl}methyl)-2-(prop-2-en-1-yl)-octahydro-1H-pyrazino[2,1-c][1,2,4]triazine-1-carboxamide compound.

BACKGROUND ART

A Wnt signaling pathway is conserved regardless of the difference in the species of organisms, and is known as an important pathway involved in the development, differentiation and maintenance of living organisms. In recent years, however, it is reported that the constitutive activation of the pathway is involved in the development of malignant transformation of fibrosis and cancer. It is known that, particularly in colorectal cancer, melanoma, endometrial cancer, liver cancer and prostate cancer, the Wnt signaling pathway can be activated constitutively by the suppressible mutation of adenomatous polyposis coli (APC) or activating mutation of β-catenin or the like. It is also known that, in pancreatic cancer, hematological cancer, liver cancer and the like, the Wnt signaling pathway can be activated after the treatment with a known anti-tumor agent.

In Non Patent Literatures 1 and 2, it is described that an excellent anti-tumor activity can be achieved by inhibiting the Wnt signaling pathway. In Non Patent Literatures 12, 13 and 14, it is described that an excellent effect on fibrosis can be achieved by inhibiting the Wnt signaling pathway. Thus, the Wnt signaling pathway has attracted attention as a novel target for the treatment of tumors or the treatment of fibrosis.

In Non Patent Literatures 3, 4, 5, 6, 7, 8, 9, 10 and 11, compounds or antibodies capable of inhibiting the Wnt signaling pathways are disclosed, and it is reported that the compounds or the antibodies can act on Tankyrase, Traf2- and Nck-interacting kinase (TNIK), Porcupine, Frizzled Receptor and the like.

Furthermore, compounds each having an octahydro-1H-pyrazino[2,1-c][1,2,4]triazine backbone are known as modulator of the Wnt signaling pathway, and the relationship between the compounds and diseases such as cancer and fibrosis is pointed out (Patent Literatures 1 to 3).

CITATION LIST

Patent Literature

[Patent Literature 1] WO 2009/051397 A
[Patent Literature 2] US 2010/0286094 A
[Patent Literature 3] WO 2009/148192 A

Non Patent Literature

[Non Patent Literature 1] Nick Barker et al., "Mining the Wnt pathway for cancer therapeutics", Nature reviews Drug discovery 2006 December; 5(12):997-1014.
[Non Patent Literature 2] Katayoon H. Emami et al., "A small molecule inhibitor of beta-catenin/CREB-binding protein transcription", Proc. Natl. Acad. Sci. USA., 2004, 101(34), p. 12682-12687.
[Non Patent Literature 3] Baozhi Chen et al., "Small molecule-mediated disruption of Wnt-dependent signaling in tissue regeneration and cancer", Nat Chem Biol., 2009, 5(2), p. 100-107.
[Non Patent Literature 4] Shih-Min A. Huang et al., "Tankyrase inhibition stabilizes axin and antagonizes Wnt signalling", Nature, 2009, 461, p. 614-620.
[Non Patent Literature 5] Lari Lehtio et al., "Tankyrases as drug targets", The FEBS Journal, 2013, 280, 3576-3593.
[Non Patent Literature 6] Miki Shitashige et al., "Traf2- and Nck-Interacting Kinase Is Essential for Wnt Signaling and Colorectal Cancer Growth", Cancer Res., 2010, 70(12), 5024-5033.
[Non Patent Literature 7] Austin Gurney et al., "Wnt pathway inhibition via the targeting of Frizzled receptors results in decreased growth and tumorigenicity of human tumors", Proc. Natl. Acad. Sci. USA., 2012, 109(29), 11717-11722.
[Non Patent Literature 8] Xiaomo Jiang et al., "Inactivating mutations of RNF43 confer Wnt dependency in pancreatic ductal adenocarcinoma", Proc. Natl. Acad. Sci. USA., 2013, 110(31), 12649-12654.
[Non Patent Literature 9] Jo Waaler et al., "Novel Synthetic Antagonists of Canonical Wnt Signaling Inhibit Colorectal Cancer Cell Growth", Cancer Res, 2011, 71(1), 197-205.
[Non Patent Literature 10] H Yao et al., "AV-65, a novel Wnt/β-catenin signal inhibitor, successfully suppresses progression of multiple myeloma in a mouse model", Blood Cancer Journal, 2011, 1, e43.
[Non Patent Literature 11] De Robertis A et al., "Identification and characterization of a small-molecule inhibitor of Wnt signaling in glioblastoma cells", Mol Cancer Ther., 2013, 12(7), 1180-1189.
[Non Patent Literature 12] Anna P Lam et al., "β-catenin signaling: a novel mediator of fibrosis and potential therapeutic target", Curr Opin Rheumatol. 2011 November; 23(6): 562-567.
[Non Patent Literature 13] Sha Hao et al., "Targeted Inhibition of β-Catenin/CBP Signaling Ameliorates Renal Interstitial Fibrosis", J. Am. Soc. Nephrol. 22: 1642-1653, 2011.
[Non Patent Literature 14] William R. Henderson, Jr. et al., "Inhibition of Wnt/β-catenin/CREB binding protein (CBP) signaling reverses pulmonary fibrosis", Proc. Natl. Acad. Sci. USA., 2010, 107(32), 14309-14314.

SUMMARY OF INVENTION

Technical Problem (6S,9aS)-N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl) hexahydro-2H-pyrazino[2,1-c][1,2,4]triazine-1(6H)-carboxamide (hereinafter referred to as "Compound 1"), which is a compound represented by the following formula, has a Wnt Pathway modulating activity.

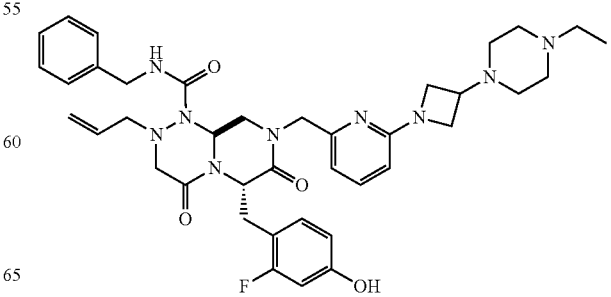

Generally, the physical properties of compounds and salts thereof and crystals thereof used as pharmaceutical products have a large effect on the bioavailability of drugs, the purity of drug substances, the pharmaceutical formulation, and the like. Therefore, the problem to be solved by the present invention is to provide a crystal of Compound 1 having a potential use as a drug substance for pharmaceutical products.

Solution to Problem

The present inventors have completed the present invention as a result of diligent efforts.
That is, the present invention provides the following [1] to [12]:
[1] A crystal of (6S,9aS)-N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1 (6H)-carboxamide.

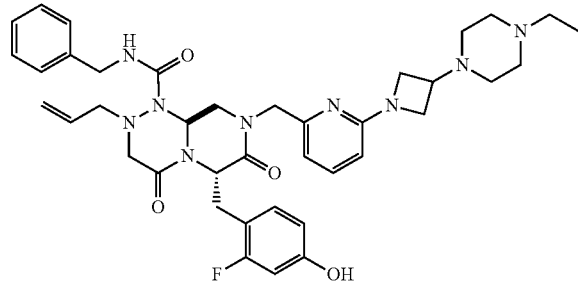

[2] The crystal according to [1], wherein the crystal has a diffraction peak at the diffraction angle (2θ±0.2°) of 5.8° in powder X-ray diffraction.
[3] The crystal according to [1], wherein the crystal has diffraction peaks at the diffraction angles (2θ±0.2°) of 5.8°, 6.4° and 10.1 θ in powder X-ray diffraction.
[4] The crystal according to [3], wherein the crystal further has diffraction peaks at the diffraction angles (2θ±0.2°) of 8.0° and 12.8° in powder X-ray diffraction.
[5] The crystal according to [4], wherein the crystal further has diffraction peaks at the diffraction angles (2θ±0.2°) of 14.2°, 16.0°, 18.9°, 19.7° and 23.1° in powder X-ray diffraction.
[6] A crystal of (6S,9aS)-N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide, wherein the crystal has a peak at the chemical shift (δ±0.5 ppm) of 154.7 ppm in solid state $^{13}$C NMR spectrum.
[7] The crystal according to [6], wherein the crystal further has peaks at the chemical shifts (δ±0.5 ppm) of 141.1 ppm and 158.1 ppm in solid state $^{13}$C NMR spectrum.
[8] The crystal according to [7], wherein the crystal further has peaks at the chemical shifts (δ±0.5 ppm) of 134.0 ppm and 165.1 ppm in solid state $^{13}$C NMR spectrum.
[9] The crystal according to [8], wherein the crystal further has peaks at the chemical shifts (δ±0.5 ppm) of 12.6 ppm, 55.5 ppm and 118.5 ppm in solid state $^{13}$C NMR spectrum.
[10] A crystal of (6S,9aS)-N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1 (6H)-carboxamide, wherein the crystal has substantially the same powder X-ray diffraction pattern as the powder X-ray diffraction pattern shown in FIG. 4.
[11] A crystal of (6S,9aS)-N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide, wherein the crystal has substantially the same $^{13}$C solid state NMR spectrum as solid state $^{13}$C NMR spectrum shown in FIG. 6.
A pharmaceutical composition comprising the crystal according to any one of [1] to [11].

Advantageous Effects of Invention

The crystal of Compound 1 according to the present invention has such properties as illustrated in Examples, and has a potential use as a drug substance for pharmaceutical products.

DESCRIPTION OF EMBODIMENTS

Figure 1:
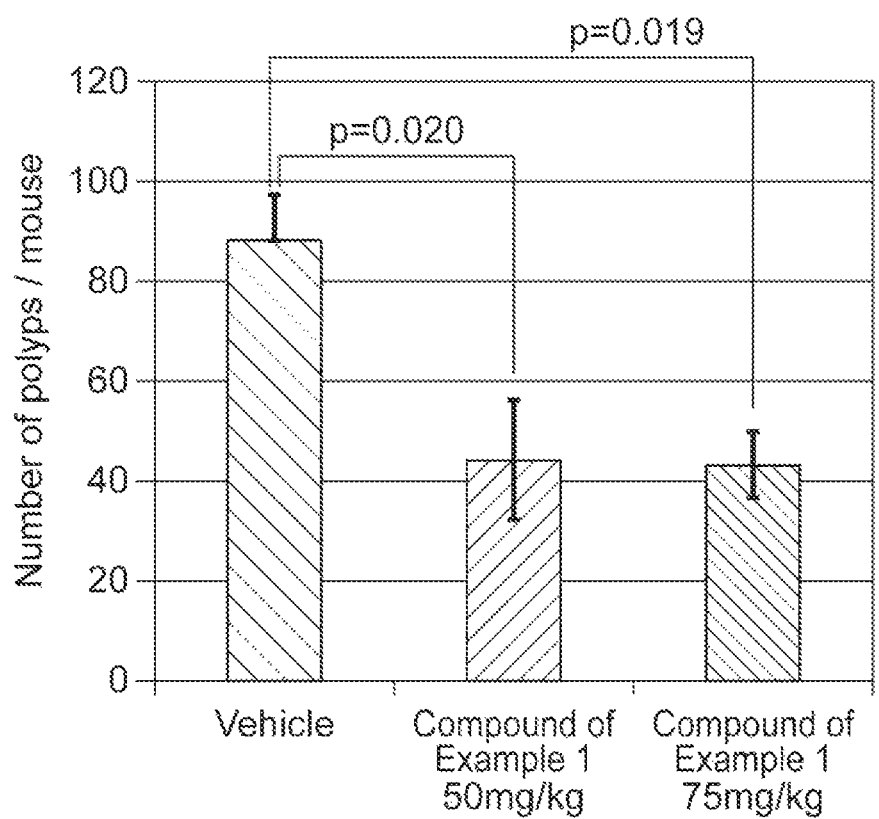
FIG. 1 shows the results of Test Example 2. The ordinate indicates the number of polyps per mouse.

In the present specification, examples of preferred crystals include:
the crystal of Compound 1 having a diffraction peak at the diffraction angle (2θ±0.2°) of 5.8° in powder X-ray diffraction;
the crystal of Compound 1 having diffraction peaks at the diffraction angles (2θ±0.2°) of 5.8°, 6.4° and 10.1° in powder X-ray diffraction;
the crystal of Compound 1 having diffraction peaks at the diffraction angles (2θ±0.2°) of 5.8°, 6.4°, 8.0°, 10.1° and 12.8° in powder X-ray diffraction; and
the crystal of Compound 1 having diffraction peaks at the diffraction angles (2θ±0.2°) of 5.8°, 6.4°, 8.0°, 10.1°, 12.8°, 14.2°, 16.0°, 18.9°, 19.7° and 23.1° in powder X-ray diffraction.
Each of the above-mentioned diffraction peaks in the powder X-ray diffraction is specific to and characteristic of the crystals of Compound 1.

Generally, as the diffraction angle (2θ) in powder X-ray diffraction may have an error within ±0.2°, it should be understood that the above-mentioned values of diffraction angles also include values within about ±0.2°. Therefore, not only crystals having completely consistent diffraction angles of peaks in powder X-ray diffraction, but also crystals having diffraction angles of peaks consistent within an error of about ±0.2° are included in the present invention.

In the present specification, for example, "have a diffraction peak at the diffraction angle (2θ±0.2°) of 5.8°" means "have a diffraction peak at the diffraction angle (2θ) of 5.6° to 6.0°" and the same applies to other diffraction angles.

Generally, even if the crystal forms are identical to each other, the peak intensity or half-width at the diffraction angle (2θ) in powder X-ray diffraction varies from one measurement to another, due to the difference in the measurement conditions and the variation in the size or shape of particles of powder crystals used as measurement samples, and constant peak intensities or half-widths are not necessarily shown. For this reason, in comparison of powder X-ray diffraction patterns, if the diffraction angles (2θ) are identical to each other but the peak intensities or half-widths thereof are different, the difference does not mean that the crystal forms of the measured crystals are different from each other. Therefore, it is meant that the crystal of the compound showing a powder X-ray diffraction pattern having such a difference with respect to the diffraction peak characteristic of the specific crystal of the present invention has the same crystal form as the crystal of the compound of the present invention. In the present specification, "have substantially the same powder X-ray diffraction pattern as the powder X-ray diffraction pattern shown in FIG. 4" means that the powder X-ray diffraction pattern having a characteristic diffraction peak is the same as the powder X-ray diffraction pattern shown in FIG. 4, not only when it is completely consistent with the powder X-ray diffraction pattern shown in FIG. 4, but also when its peak intensity or half-width is different or it is consistent within an error range of about ±0.2° with the powder X-ray diffraction pattern shown in FIG. 4. Therefore, it is meant that all crystals having such powder X-ray diffraction patterns are the same crystals as the crystal of the present invention.

In the present specification, examples of preferred crystals include:

the crystal of Compound 1 having a peak at the chemical shift (δ±0.5 ppm) of 154.7 ppm in solid state $^{13}$C NMR spectrum;

the crystal of Compound 1 having peaks at the chemical shifts (δ±0.5 ppm) of 141.1 ppm, 154.7 ppm and 158.1 ppm in solid state $^{13}$C NMR spectrum;

the crystal of Compound 1 having peaks at the chemical shifts (δ±0.5 ppm) of 134.0 ppm, 141.1 ppm, 154.7 ppm, 158.1 ppm and 165.1 ppm in solid state $^{13}$C NMR spectrum; and the crystal of Compound 1 having peaks at the chemical shifts (δ±0.5 ppm) of 12.6 ppm, 55.5 ppm, 118.5 ppm, 134.0 ppm, 141.1 ppm, 154.7 ppm, 158.1 ppm and 165.1 ppm in solid state $^{13}$C NMR spectrum.

Each of the above-mentioned peaks in the solid state $^{13}$C NMR spectrum is specific to and characteristic of the crystal of Compound 1.

In the present specification, "have the peaks at the chemical shifts (δ±0.5 ppm) of 12.6 ppm, 55.5 ppm, 118.5 ppm, 134.0 ppm, 141.1 ppm, 154.7 ppm, 158.1 ppm and 165.1 ppm" means "have the substantially equivalent peaks to the peaks at the chemical shifts (δ±0.5 ppm) of 12.6 ppm, 55.5 ppm, 118.5 ppm, 134.0 ppm, 141.1 ppm, 154.7 ppm, 158.1 ppm and 165.1 ppm, respectively, when solid state $^{13}$C NMR spectroscopy is carried out under normal conditions or under substantially the same conditions as those described in the present specification".

Figure 6:
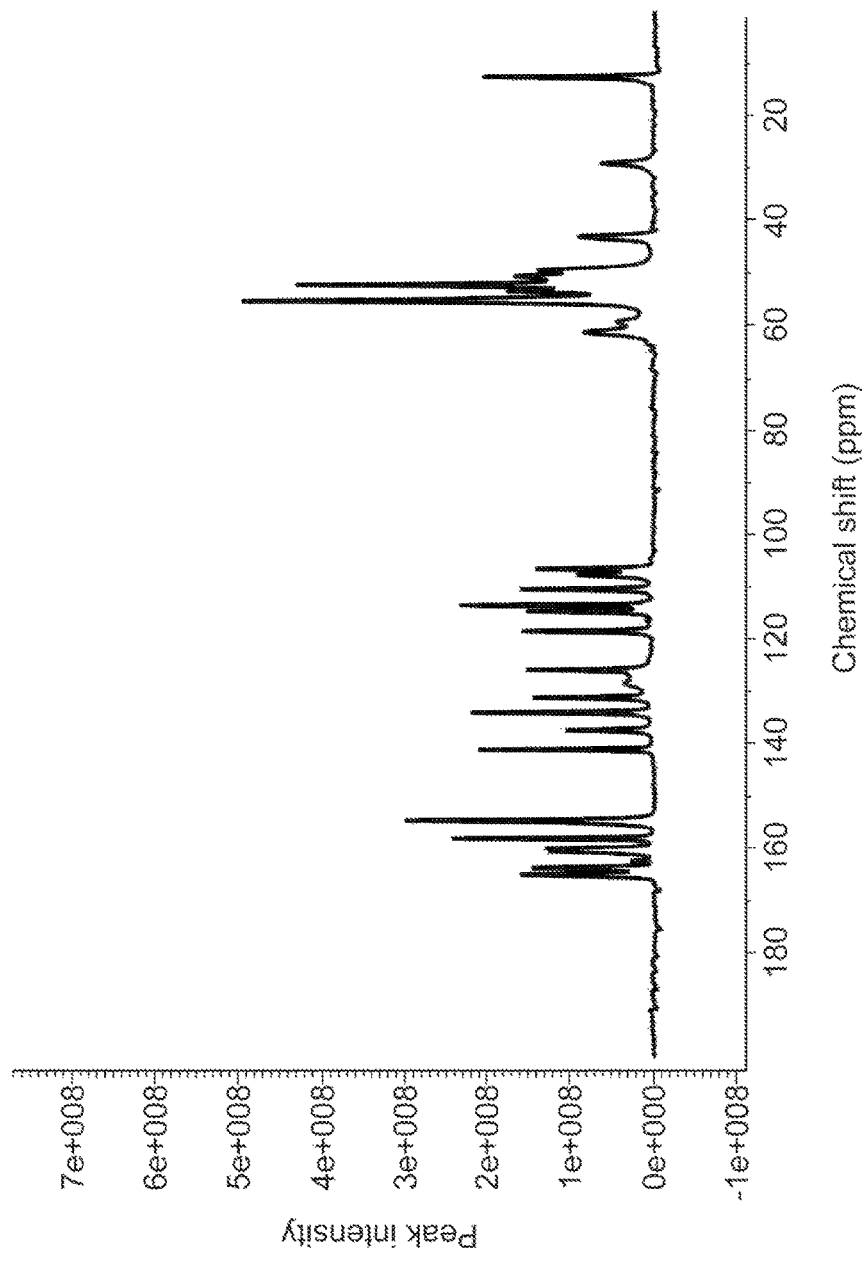
FIG. 6 is the solid state $^{13}$C NMR spectrum of the crystal of Compound 1 in Test Example 6. The abscissa indicates the chemical shift (δ), and the ordinate indicates the peak intensity.

In determining whether or not to "have the substantially equivalent peaks", generally, as the chemical shift (δ) in solid state $^{13}$C NMR spectrum may have an error within ±0.5 ppm, it should be understood that the above-mentioned values of chemical shifts also include values within about ±0.5 ppm. Therefore, not only crystals having the completely consistent chemical shifts in $^{13}$C solid state NMR spectrum, but also crystals having the chemical shifts consistent within an error of about ±0.5 ppm are included in the present invention. For this reason, in the present specification, for example, "have a peak at the chemical shift (δ±0.5 ppm) of 12.6 ppm" means "have a peak at the chemical shift (δ) of 12.1 ppm to 13.1 ppm", and the same applies to other chemical shifts in solid state $^{13}$C NMR spectrum. Furthermore, "crystal having substantially the same solid state $^{13}$C NMR spectrum as shown in FIG. 6" means that, not only when the solid state $^{13}$C NMR spectrum having a peak at a certain chemical shift is completely consistent with the solid state $^{13}$C NMR spectrum shown in FIG. 6, but also when its peak intensity is different or its characteristic peak is consistent within an error range of about ±0.5 ppm, the crystal is a crystal having the same solid state $^{13}$C NMR spectrum as shown in FIG. 6. Therefore, it is meant that all crystals having such a solid state $^{13}$C NMR spectrum are the same crystals as the crystal of the present invention.

Hereinafter, a process for producing the crystal of Compound 1 and the like which is an embodiment of the present invention will be described.

Production of Compound 1

Compound 1 can be produced by the process described in Examples and Production Examples as mentioned below.

Process for Producing the Crystal of Compound 1

The crystal of Compound 1 can be produced by the above-mentioned process for producing Compound 1, or can be produced by heating and dissolving Compound 1 in a solvent and cooling it under stirring to crystallize it.

Compound 1 used for crystallization may be in any form, may be a solvate or hydrate or anhydrate thereof, may be amorphous or crystalline (including those composed of a plurality of polymorphs), and may be any mixture thereof, but is preferably an anhydrate thereof.

Examples of the solvent for crystallization include, for example, alcohol-based solvents such as methanol, ethanol, 1-propanol and 2-propanol; acetonitrile; amide-based solvents such as N,N-dimethylformamide; ester-based solvents such as ethyl acetate and isopropyl acetate; saturated hydrocarbon-based solvents such as hexane and heptane; ketone-based solvents such as acetone and 2-butanone; ether-based solvents such as t-butyl methyl ether; or water. These solvents may be used alone or in a mixture of two or more thereof. When carrying out crystallization in a mixture of two or more solvents, it is preferable to use, for example, a combination of heptane and 1-propanol.

The amount of the solvent to be used can be appropriately selected with the lower limit being the amount at or above which Compound 1 is dissolved by heating or the amount at or above which the suspension thereof can be stirred and with the upper limit being the amount at or below which the yield of crystal is not significantly decreased.

The crystal obtained by the above process has a single crystalline form. This crystal form is stable, does not readily transit to other crystalline forms or amorphous form, has good physical properties, and is also suitable for the formulation.

In the crystallization, a seed crystal (such as the desired crystal of Compound 1) may or may not be added. The temperature at which seed crystals are added is not particularly limited, but is preferably 0 to 100° C.

For the temperature at which Compound 1 is heated to be dissolved, the temperature at which Compound 1 is dissolved may be appropriately selected depending on the solvent, but is preferably in the range of from 50° C. to the temperature at which a recrystallization solvent begins to reflux, and more preferably 60 to 100° C.

As crystals containing different aspects of crystals (polymorphs) are given when quenched, cooling at the time of crystallization is desirably carried out by appropriately adjusting the cooling rate in consideration of the influence on the quality and grain size of the crystal, and is preferably for example, at a cooling rate of 5 to 40° C./hour. It is more preferably at a cooling rate of 5 to 25° C./hour.

The final crystallization temperature can be appropriately selected depending on the yield and quality of the crystal and the like and is preferably from −25 to 30° C.

The crystallized crystal is separated by a usual filtration operation, and the crystal separated by filtration can be washed with a solvent as appropriate and further dried to obtain the desired crystal. As the solvent used for washing the crystal, the same solvent as the crystallization solvent can be used. Examples of such a solvent preferably include, for example, ethanol, acetone, 2-butanone, ethyl acetate, diethyl ether, t-butyl methyl ether, hexane and heptane. These solvents may be used alone or in a mixture of two or more thereof.

The crystal separated by the filtration operation can be dried by leaving it in the atmosphere or under a nitrogen gas as appropriate, or by heating.

For the time of drying, the time by which the residual solvent falls below a predetermined amount may be appropriately selected depending on the production amount, the drying apparatus, the drying temperature and the like. Drying can be carried out under forced-air condition or under reduced pressure. The degree of reduced pressure may be appropriately selected depending on the production amount, the drying apparatus, the drying temperature and the like. After drying, the obtained crystal can also be left in the atmosphere as appropriate.

Pharmaceutical compositions can be prepared by adding pharmaceutically acceptable additives to the crystal of Compound 1, as appropriate. Examples of the dosage form of the pharmaceutical composition include oral preparations (tablets, granules, powders, capsules, syrups, etc.), injectable preparations (for intravenous administration, for intramuscular administration, for subcutaneous administration, for intraperitoneal administration, etc.), and preparations for external applications (transdermal absorption preparations (ointments, patches, etc.), eye drops, nose drops, suppositories, etc.).

These solid preparations such as tablets, capsules, granules and powders can contain the crystal of Compound 1 usually in an amount of 0.001 to 99.5% by mass, preferably 0.001 to 90% by mass.

In the case of preparing an oral solid preparation, an excipient, a binder, a disintegrator, a lubricant, a colorant and the like are added to the crystal of Compound 1, as appropriate to prepare tablets, granules, powders or capsules by a conventional method. Tablets, granules, powders, capsules and the like may also be coated as appropriate.

The dose of the medicine according to the present invention is generally varied depending on the bodily conditions, ages, sexes, body weights and the like, and may be an enough amount to develop a desired effect. For example, in the case of a human adult, about 0.1 to 5000 mg (preferably 0.5 to 1000 mg) per day is administered one time daily or every several days or in 2 to 6 divided doses daily.

EXAMPLES

The crystal of Compound 1 according to the present invention can be produced by the methods described in Production Examples and Examples as mentioned below. However, these examples are only for illustrative purposes and the crystal of the compound according to the present invention is not limited to the specific examples mentioned below in any way.

In Production Examples and Examples, unless specifically mentioned otherwise, the silica gel for purification by using silica gel column chromatography was YMC GEL SILICA (YMC Co., Ltd, catalog code: SL06I52W), the silica gel for purification by using NH silica gel column chromatography was NH silica gel (Fuji Silysia Chemical LTD., catalog code: DM2035), the silica gel for purification by using ODS silica gel column chromatography was YAMAZEN GEL ODS-SM (YAMAZEN Corporation, catalog codes: W113, W116, etc.), the TLC plate for purification by using silica gel thin-layer chromatography was TLC Silica gel 60F$_{254}$ (Merck KGaA, catalog code: 1.05715.0001), and the TLC plate for purification by using NH silica gel thin-layer chromatography was NH SILICA GEL TLC plate (Fuji Silysia Chemical LTD., catalog code: T050908).

The abbreviations used herein are as follows:
NMP: N-methylpyrrolidinone
THF: tetrahydrofuran
HATU: O-(7-azabenzotriazol-1-yl)-N,N,N,N-tetramethyluronium hexafluorophosphate
HBTU: O-(benzotriazol-1-yl)-N,N,N,N-tetramethyluronium hexafluorophosphate
TFA: trifluoroacetic acid
DMF: N,N-dimethylformamide
DMSO: dimethylsolfoxide Chemical shifts of $^1$H-NMR (proton nuclear magnetic resonance) spectra are recorded in δ units (ppm) relative to tetramethylsilane and coupling constants are recorded in hertz (Hz). The abbreviations of the splitting pattern are as follows: s: singlet; d: doublet; t: triplet; q: quartet; m: multiplet; and br: broad.

Example 1

(6S,9aS)-N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide

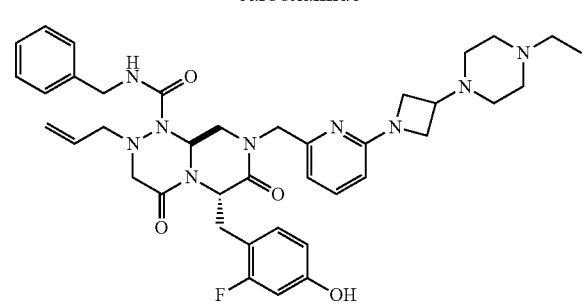

To a mixed solution of (6S,9aS)-N-benzyl-6-((2-fluoro-4-hydroxyphenyl)methyl)-8-((6-fluoropyridin-2-yl)methyl)-4,7-dioxo-2-(prop-2-en-1-yl)-octahydro-1H-pyrazino[2,1-c][1,2,4]triazine-1-carboxamide (397 mg, 0.689 mmol) described in Production Example 1-1-6 and NMP (10 mL) was added a mixture (1.16 g) of 1-(azetidin-3-yl)-4-ethylpiperazine and benzylbenzene described in Production Example 1-3-2 at room temperature. The resultant mixture was irradiated with a microwave at 140° C. for 12 hours. The reaction mixture was cooled to room temperature, water was then added thereto, then the resultant solution was extracted with ethyl acetate, and an organic layer was washed with saturated brine. The organic layer was dried over anhydrous magnesium sulfate and then filtrated. The solvent was evaporated under a reduced pressure, and the resultant residue was purified by silica gel column chromatography (methanol) and then further purified by NH silica gel column chromatography (ethyl acetate:methanol=20:1) to give the title compound (402 mg, yield: 80%).

$^1$H-NMR Spectrum (400 MHz, CDCl$_3$) δ (ppm): 1.00 (3H, t, J=6.8 Hz), 2.10-2.65 (10H, m), 3.10-3.21 (2H, m), 3.41-3.74 (8H, m), 3.84-3.89 (1H, m), 3.95-4.05 (2H, m), 4.17-4.23 (2H, m), 4.51 (1H, dd, J=6.8 Hz, 15.6 Hz), 4.95 (1H, d, J=13.6 Hz), 5.20-5.30 (3H, m), 5.50-5.60 (1H, m), 5.70-5.80 (1H, m), 5.82-5.87 (1H, m), 6.24 (1H, d, J=8.0 Hz), 6.41 (1H, dd, J=2.0 Hz, 11.2 Hz), 6.47 (1H, dd, J=8.8 Hz, 8.8 Hz), 6.69 (1H, d, J=7.2 Hz), 6.80-6.86 (1H, m), 7.20-7.31 (3H, m), 7.35-7.46 (3H, m).

ESI-MS (m/z): 726.57 [M+H]$^+$.

Production Example 1-1-1

(2,2-Diethoxyethyl)((6-fluoropyridin-2-yl)methyl)amine

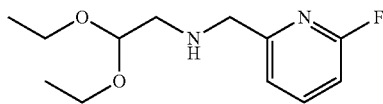 [SMILES: CCOC(CNCc1cccc(F)n1)OCC]

To a mixed solution of a commercially available product of 2,2-diethoxyethan-1-amine (926 μL, 6.39 mmol), THF (10.0 mL) and acetic acid (1.00 mL) was added a commercially available product of 6-fluoropyridine-2-carbaldehyde (800 mg, 6.39 mmol) at room temperature. The resultant mixture was stirred at room temperature for 25 minutes. Subsequently, sodium triacetoxyborohydride (2.71 g, 12.8 mmol) was added to the reaction mixture at room temperature and then stirred for 1 hour and 10 minutes. To the reaction mixture was added sodium hydrogen carbonate and water to terminate the reaction. The resultant solution was extracted with ethyl acetate. An organic layer was dried over anhydrous magnesium sulfate and then filtrated. The solvent was evaporated under a reduced pressure, and the resultant residue was purified by NH silica gel column chromatography (heptane:ethyl acetate=1:1), and was then further purified by silica gel column chromatography (ethyl acetate:methanol=20:1) to give the title compound (1.14 g, yield: 74%).

$^1$H-NMR Spectrum (400 MHz, CDCl$_3$) δ (ppm): 1.22 (6H, t, J=7.2 Hz), 2.76 (2H, d, J=5.5 Hz), 3.50-3.61 (2H, m), 3.65-3.76 (2H, m), 3.89 (2H, s), 4.64 (1H, t, J=5.5 Hz), 6.80 (1H, dd, J=2.8 Hz, 8.2 Hz), 7.22 (1H, dd, J=2.4 Hz, 7.3 Hz), 7.74 (1H, q, J=7.9 Hz).

Production Example 1-1-2

9H-Fluoren-9-ylmethyl N-((1 S)-2-(4-(benzyloxy)-2-fluorophenyl)-1-(2,2-diethoxyethyl)((6-fluoropyridin-2-yl)methyl)carbamoyl)ethyl)carbamate

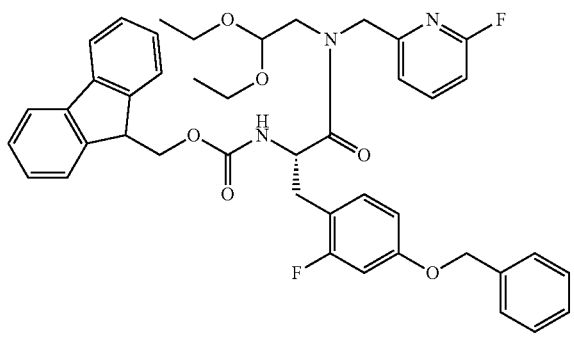 [SMILES: CCOC(CN(Cc1cccc(F)n1)C(=O)[C@H](Cc1ccc(OCc2ccccc2)cc1F)NC(=O)OCC1c2ccccc2-c2ccccc21)OCC]

To a mixed solution of (2,2-diethoxyethyl)((6-fluoropyridin-2-yl)methyl)amine (3.50 g, 14.4 mmol) described in Production Example 1-1-1 and dichloromethane (25 mL) were added (2S)-3-(4-(benzyloxy)-2-fluorophenyl)-2-(((9H-fluoren-9-ylmethoxy)carbonyl)amino)propanoic acid (7.76 g, 15.1 mmol) described in Production Example 1-2-7, N-methylmorpholine (2.06 mL, 18.7 mmol) and HATU (6.04 g, 15.8 mmol) at room temperature. The resultant mixture was stirred at room temperature for 13 hours. Sodium hydrogen carbonate and water were added to the reaction mixture, and the resultant solution was extracted with dichloromethane. An organic layer was dried over anhydrous magnesium sulfate and then filtrated. The solvent was evaporated under a reduced pressure to give a crude product (14.4 g) of the title compound. The product was used in the subsequent reaction without further purification.

ESI-MS (m/z): 758.50 [M+Na]$^+$.

Production Example 1-1-3

(2S)-2-Amino-3-(4-(benzyloxy)-2-fluorophenyl)-N-(2,2-diethoxyethyl)-N-((6-fluoropyridin-2-yl)methyl)propanamide

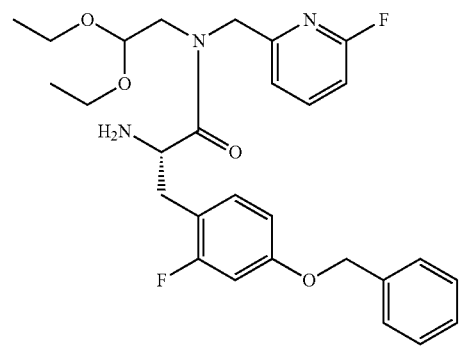 [SMILES: CCOC(CN(Cc1cccc(F)n1)C(=O)[C@@H](N)Cc1ccc(OCc2ccccc2)cc1F)OCC]

To a mixed solution of 9H-fluoren-9-ylmethyl N-((1S)-2-(4-(benzyloxy)-2-fluorophenyl)-1-((2,2-diethoxyethyl)((6-fluoropyridin-2-yl)methyl)carbamoyl)ethyl)carbamate described in Production Example 1-1-2 (14.4 g) and THF (30 mL) was added diethylamine (5.27 mL, 50.4 mmol) at room temperature. The resultant mixture was stirred at room temperature for 2 hours. The reaction mixture was concentrated under a reduced pressure, methanol, water and heptane were added to the residue, and the resultant mixture was partitioned. An aqueous layer was washed with heptane, and was then concentrated under a reduced pressure. Water was added to the residue, and the resultant solution was extracted with ethyl acetate. An organic layer was dried over anhydrous magnesium sulfate and then filtrated. The solvent was evaporated under a reduced pressure, and the resultant residue was purified by NH silica gel column chromatography (heptane:ethyl acetate=1:1, and then ethyl acetate) to give the title compound (6.87 g, yield: 93%).

ESI-MS (m/z): 514.32 [M+H]⁺.

Production Example 1-1-4

(2S)-2-(2-(((Benzylcarbamoyl)amino)(prop-2-en-1-yl)amino)acetamido)-3-(4-(benzyloxy)-2-fluorophenyl)-N-(2,2-diethoxyethyl)-N-((6-fluoropyridin-2-yl)methyl)propanamide

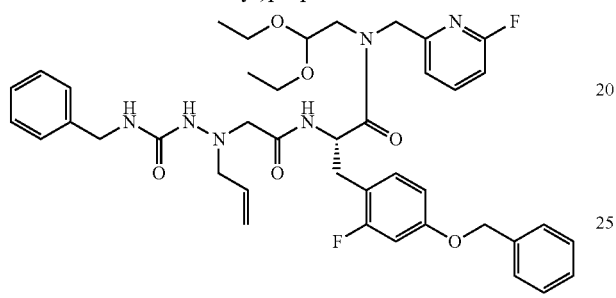

To a mixed solution of (2S)-2-amino-3-(4-(benzyloxy)-2-fluorophenyl)-N-(2,2-diethoxyethyl)-N-((6-fluoropyridin-2-yl)methyl)propanamide (4.87 g, 9.48 mmol) described in Production Example 1-1-3 and dichloromethane (100 mL) were added a known substance (WO2009/148192) 2-(((benzylcarbamoyl)amino)(prop-2-en-1-yl)amino)acetic acid (2.62 g, 9.95 mmol), triethylamine (2.64 mL, 19.0 mmol) and HBTU (3.96 g, 10.4 mmol) at room temperature. The resultant mixture was stirred at room temperature for 1 hour. The reaction mixture was concentrated under a reduced pressure, and the resultant residue was purified by NH silica gel column chromatography (ethyl acetate and then ethyl acetate:methanol=30:1) to give the title compound (7.28 g, yield: quantitative).

ESI-MS (m/z): 759.43 [M+H]*.

Production Example 1-1-5

(6S,9aS)—N-Benzyl-6-((4-(benzyloxy)-2-fluorophenyl)methyl)-8-((6-fluoropyridin-2-yl)methyl)-4,7-dioxo-2-(prop-2-en-1-yl)-octahydro-1H-pyrazino[2,1-c][1,2,4]triazine-1-carboxamide

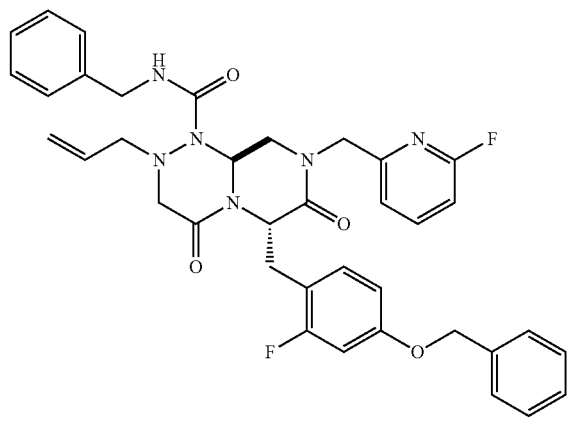

A mixed solution of (2S)-2-(2-(((benzylcarbamoyl)amino)(prop-2-en-1-yl)amino)acetamido)-3-(4-(benzyloxy)-2-fluorophenyl)-N-(2,2-diethoxyethyl)-N-((6-fluoropyridin-2-yl) methyl)propanamide (7.28 g, 9.48 mmol) described in Production Example 1-1-4 and formic acid (50 mL) was stirred at room temperature for 15 hours and 15 minutes. The reaction mixture was concentrated under a reduced pressure, an aqueous ammonia solution was added to the residue, and the resultant solution was extracted with ethyl acetate. An organic layer was dried over anhydrous magnesium sulfate and then filtrated. The solvent was evaporated under a reduced pressure, and the resultant residue was purified by NH silica gel column chromatography (heptane:ethyl acetate=1:1) to give the title compound (5.04 g, yield: 80%).

ESI-MS (m/z): 667.39 [M+H]⁺.

Production Example 1-1-6

(6S,9aS)—N-Benzyl-6-((2-fluoro-4-hydroxyphenyl)methyl)-8-((6-fluoropyridin-2-yl)methyl)-4,7-dioxo-2-(prop-2-en-1-yl)-octahydro-1H-pyrazino[2,1-c][1,2,4]triazine-1-carboxamide

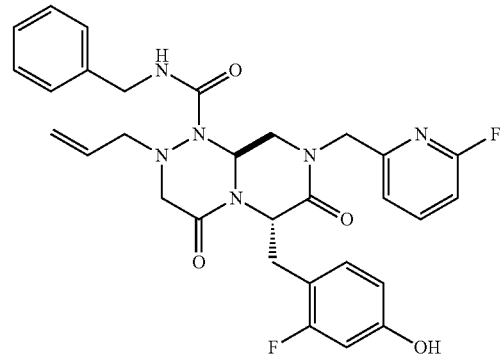

To a mixed solution of (6S,9aS)-N-benzyl-6-((4-(benzyloxy)-2-fluorophenyl)methyl)-8-((6-fluoropyridin-2-yl)methyl)-4,7-dioxo-2-(prop-2-en-1-yl)-octahydro-1H-pyrazino[2,1-c][1,2,4]triazine-1-carboxamide (5.04 g, 7.56 mmol) described in Production Example 1-1-5 and TFA (20 mL) was added thioanisole (3.55 mL, 30.2 mmol) at room temperature. The resultant mixture was stirred at room temperature for 13 hours and 50 minutes. The reaction mixture was concentrated under a reduced pressure, sodium hydrogen carbonate and water were added to the residue, and the resultant solution was extracted with ethyl acetate. An organic layer was dried over anhydrous magnesium sulfate and then filtrated. The solvent was evaporated under a reduced pressure, and the resultant residue was purified by NH silica gel column chromatography (ethyl acetate:methanol=20:1) to give the title compound (4.34 g, yield: quantitative).

ESI-MS (m/z): 577.31 [M+H]⁺.

Production Example 1-2-1

Methyl (2S)-2-(((9H-fluoren-9-ylmethoxy)carbonyl)amino)-3-hydroxypropanoate

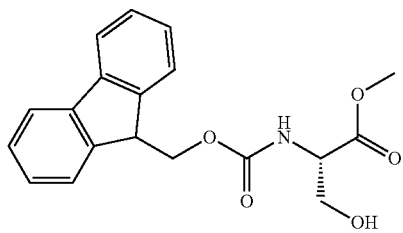 [SMILES: COC(=O)[C@H](CO)NC(=O)OCC1c2ccccc2-c2ccccc21]

To a mixed solution of a commercially available product of L-serine methyl ester hydrochloride (10.0 g, 64.3 mmol), 1,4-dioxane (15 mL) and water (90 mL) was added sodium hydrogen carbonate (10.8 g, 129 mmol) at room temperature. The resultant mixture was stirred at room temperature for 15 minutes. Subsequently, a solution of 2,5-dioxopyrrolidin-1-yl 9H-fluoren-9-ylmethylcarbonate (21.7 g, 64.3 mmol) in 1,4-dioxane (60 mL) was added to the resultant solution at room temperature, and the resultant mixture was stirred at room temperature for 14 hours. Water was added to the reaction mixture, the resultant solution was extracted with ethyl acetate three times, and a combined organic layer was washed with water and saturated brine. An organic layer was dried over anhydrous magnesium sulfate and then filtrated. The solvent was evaporated under a reduced pressure, diethyl ether and heptane were added to the resultant residue, and a precipitate was collected by filtration to give the title compound (22.3 g, yield: quantitative).

$^1$H-NMR Spectrum (400 MHz, CDCl$_3$) δ (ppm): 2.00-2.15 (1H, m), 3.81 (3H, s), 3.89-4.07 (2H, m), 4.20-4.28 (1H, in), 4.39-4.53 (3H, m), 5.63-5.74 (1H, m), 7.29-7.37 (2H, m), 7.38-7.46 (2H, m), 7.55-7.65 (2H, m), 7.74-7.82 (2H, m).

Production Example 1-2-2

Methyl (2S)-2-(((9H-fluoren-9-ylmethoxy)carbonyl)amino)-3-(((4-methylbenzene)sulfonyl)oxy)propanoate

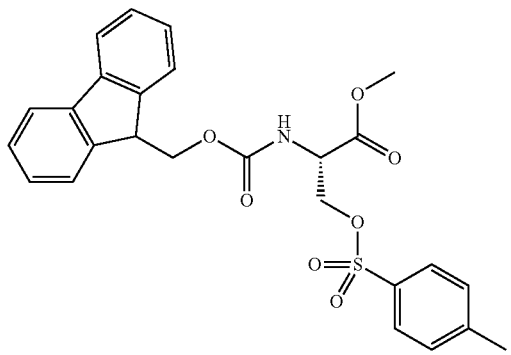 [SMILES: COC(=O)[C@H](COS(=O)(=O)c1ccc(C)cc1)NC(=O)OCC1c2ccccc2-c2ccccc21]

To a mixed solution of methyl (2S)-2-(((9H-fluoren-9-ylmethoxy)carbonyl)amino)-3-hydroxypropanoate (5.00 g, 14.6 mmol) described in Production Example 1-2-1 and pyridine (25 mL) were added 4-dimethylaminopyridine (18.0 mg, 0.146 mmol) and p-toluenesulfonyl chloride (5.58 g, 29.3 mmol) at 0° C., and the resultant mixture was stirred at 0° C. for 7 hours. Water was added to the reaction mixture, and the resultant solution was extracted with ethyl acetate two times. A combined organic layer was washed with 1 N hydrochloric acid three times, then with a saturated aqueous sodium hydrogen carbonate solution, and then with saturated brine. An organic layer was dried over anhydrous magnesium sulfate and then filtrated. The solvent was evaporated under a reduced pressure, then ethyl acetate, diethyl ether and heptane were added to the resultant residue, and then a precipitate was collected by filtration to give the title compound (6.20 g, yield: 85%).

$^1$H-NMR Spectrum (400 MHz, CDCl$_3$) δ (ppm): 2.37 (3H, s), 3.74 (3H, s), 4.16-4.23 (1H, m), 4.23-4.31 (1H, m), 4.32-4.40 (2H, m), 4.41-4.48 (1H, m), 4.54-4.62 (1H, m), 5.63-5.66 (1H, m), 7.26-7.37 (4H, m), 7.38-7.45 (2H, m), 7.56-7.64 (2H, m), 7.72-7.81 (4H, m).

Production Example 1-2-3

Methyl (2R)-2-(((9H-fluoren-9-ylmethoxy)carbonyl)amino)-3-iodopropanoate

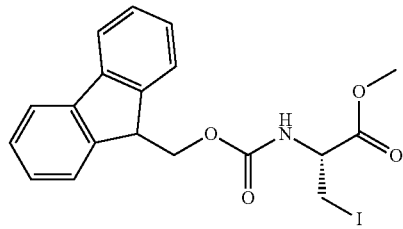 [SMILES: COC(=O)[C@H](CI)NC(=O)OCC1c2ccccc2-c2ccccc21]

To a mixed solution of methyl (2S)-2-(((9H-fluoren-9-ylmethoxy)carbonyl)amino)-3-(((4-methylbenzene)sulfonyl)oxy)propanoate (6.20 g, 12.5 mmol) described in Production Example 1-2-2 and acetone (50 mL) was added sodium iodide (9.38 g, 62.6 mmol) at room temperature. The resultant mixture was stirred at room temperature for 90 hours and 50 minutes. The reaction mixture was filtrated, and a filtrate was concentrated under a reduced pressure. Water was added to the residue, and the resultant solution was extracted with ethyl acetate. An organic layer was washed with water, then with a saturated aqueous sodium thiosulfate solution, and then saturated brine. An organic layer was dried over anhydrous magnesium sulfate and then filtrated. The solvent was evaporated under a reduced pressure, then diethyl ether and heptane were added to the resultant residue, and a precipitate was collected by filtration to give the title compound (3.82 g, yield: 68%).

$^1$H-NMR Spectrum (400 MHz, CDCl$_3$) δ (ppm): 3.55-3.66 (2H, m), 3.84 (3H, s), 4.20-4.30 (1H, m), 4.35-4.48 (2H, m), 4.56-4.62 (1H, m), 5.63-5.72 (1H, m), 7.30-7.37 (2H, m), 7.38-7.45 (2H, m), 7.62 (2H, d, J=7.2 Hz), 7.78 (2H, d, J=7.5 Hz).

Production Example 1-2-4

4-(Benzyloxy)-1-bromo-2-fluorobenzene

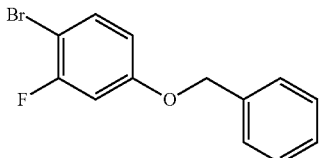

To a mixed solution of a commercially available product of 4-bromo-3-fluorophenol (15.0 g, 78.5 mmol) and DMF (30 mL) were added potassium carbonate (21.7 g, 157 mmol) and benzyl bromide (10.2 mL, 86.4 mmol) at room temperature, and the resultant mixture was stirred at room temperature for 20 minutes and then at 70° C. for 40 minutes. The reaction mixture was cooled to room temperature, then water was added to the reaction mixture, and the resultant solution was extracted with ethyl acetate. An organic layer was washed with water and then with saturated brine. An organic layer was dried over anhydrous magnesium sulfate and then filtrated. The solvent was evaporated under a reduced pressure, and the resultant residue was purified by silica gel column chromatography (heptane:ethyl acetate=5:1) to give the title compound (22.7 g, yield: quantitative).

$^1$H-NMR Spectrum (400 MHz, CDCl$_3$) δ (ppm): 5.04 (2H, s), 6.65-6.72 (1H, m), 6.75-6.80 (1H, m), 7.30-7.45 (6H, m).

Production Example 1-2-5

4-(Benzyloxy)-2-fluoro-1-iodobenzene

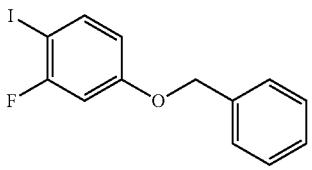 [SMILES: Fc1cc(OCc2ccccc2)ccc1I]

To a mixed solution of 4-(benzyloxy)-1-bromo-2-fluorobenzene (187 g, 665 mmol) described in Production Example 1-2-4 and 1,4-dioxane (300 mL) were added copper iodide (I) (12.6 g, 66.1 mmol), sodium iodide (200 g, 1.33 mol) and N,N'-dimethylethylenediamine (14.0 mL, 132 mmol) at room temperature, and the resultant mixture was stirred under a nitrogen atmosphere at 110 to 115° C. for 19 hours. The reaction mixture was cooled to room temperature, then water and ethyl acetate were added to the reaction mixture, the resultant mixture was filtrated using Celite, and a filtrate was partitioned between aqueous layer and organic layer. The aqueous layer was extracted with ethyl acetate. The combined organic layers were filtrated using a glass filter having silica gel laid thereon. The silica gel was washed with ethyl acetate, organic layers obtained were combined, and the solvent was evaporated under a reduced pressure. The resultant residue was purified by silica gel column chromatography (heptane:ethyl acetate=7:1 and then 4:1) to give the title compound (195 g, yield: 89%).

$^1$H-NMR Spectrum (400 MHz, CDCl$_3$) δ (ppm): 5.04 (2H, s), 6.57-6.62 (1H, m), 6.73 (1H, dd, J=2.8 Hz, 10.0 Hz), 7.31-7.43 (5H, m), 7.55-7.60 (1H, m).

Production Example 1-2-6

Methyl (2S)-3-(4-(benzyloxy)-2-fluorophenyl)-2-(((9H-fluoren-9-ylmethoxy)carbonyl)amino)propanoate

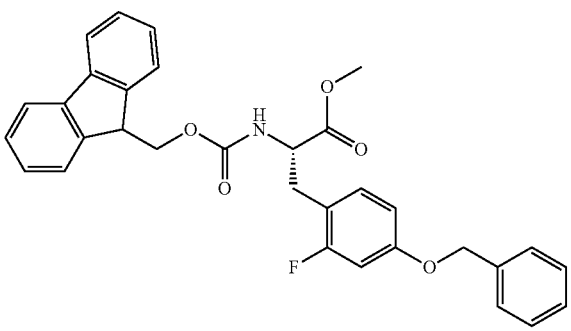 [SMILES: COC(=O)[C@H](Cc1ccc(OCc2ccccc2)cc1F)NC(=O)OCC1c2ccccc2-c2ccccc21]

A zinc powder (51.6 g, 789 mmol) was added to 1 N hydrochloric acid (100 mL), the resultant mixture was sonicated and then allowed to stand, and then a supernatant was removed therefrom. This procedure was repeated two times. Water (300 mL) was added to the resultant zinc residue, the resultant solution was stirred and then allowed to stand, and then a supernatant was removed therefrom. This procedure was repeated three times. Acetone (300 mL) was added to the resultant product, the mixture was stirred and then allowed to stand, a supernatant was removed therefrom, then diethyl ether (300 mL) was added to the solution, the resultant solution was stirred and then allowed to stand, a supernatant was removed therefrom, and a residue was then dried under reduced pressure to give activated zinc. To the activated zinc were added DMF (120 mL) and iodine (3.36 g, 13.2 mmol) under a nitrogen atmosphere at room temperature. The resultant mixture was stirred at room temperature for 45 minutes. To the reaction mixture was added a solution of methyl (2R)-2-(((9H-fluoren-9-ylmethoxy)carbonyl)amino)-3-iodopropanoate (120 g, 266 mmol) described in Production Example 1-2-3 in DMF (500 mL) over 30 minutes under a nitrogen atmosphere at room temperature. The resultant mixture was stirred at room temperature for 40 minutes. To the reaction mixture were added 4-(benzyloxy)-2-fluoro-1-iodobenzene (104 g, 318 mmol) described in Production Example 1-2-5, tris(dibenzylideneacetone)palladium (0) (6.00 g, 6.55 mmol) and 2-dicyclohexylphosphino-2',6'-dimethoxybiphenyl (5.40 g, 13.2 mmol) under a nitrogen atmosphere at room temperature. The resultant mixture was stirred at room temperature for 20 hours and 40 minutes. Water and ethyl acetate were added to the reaction mixture, and the resultant solution was filtrated using Celite. A filtrate was partitioned, and an aqueous layer was further extracted with ethyl acetate three times. A combined organic layer was washed with water and saturated brine. An organic layer was dried over anhydrous magnesium sulfate and then filtrated. The solvent was evaporated under a reduced pressure, then diethyl ether (1.00 L) and heptane (1.00 L) were added to the resultant residue, and then a precipitate was collected by filtration. Diethyl ether (500 mL) and heptane (500 mL) were added to the filtrated solid, and a precipitate was collected by filtration to give the title compound (107 g, yield: 77%).

$^1$H-NMR Spectrum (400 MHz, CDCl$_3$) (ppm): 3.03-3.20 (2H, m), 3.75 (3H, s), 4.20 (1H, t, J=6.6 Hz), 4.25-4.38 (1H, m), 4.43 (1H, dd, J=7.1 Hz, 10.4 Hz), 4.58-4.70 (1H, m), 4.99 (2H, s), 5.33 (1H, d, J=8.4 Hz), 6.63-6.72 (2H, m), 6.94-7.03 (1H, m), 7.26-7.48 (9H, m), 7.52-7.62 (2H, m), 7.77 (2H, d, J=7.7 Hz).

Production Example 1-2-7

(2S)-3-(4-(Benzyloxy)-2-fluorophenyl)-2-(((9H-fluoren-9-ylmethoxy)carbonyl)amino)propanoic Acid

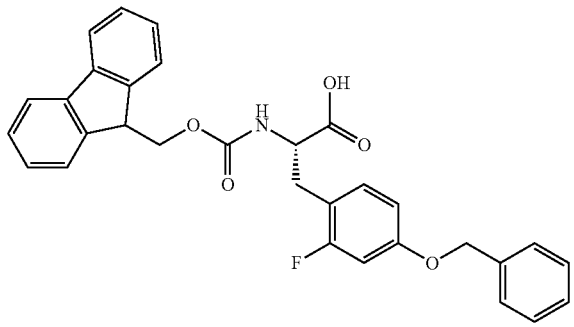 [SMILES: O=C(N[C@@H](Cc1ccc(OCc2ccccc2)cc1F)C(=O)O)OCC1c2ccccc2-c2ccccc21]

To a mixed solution of methyl (2S)-3-(4-(benzyloxy)-2-fluorophenyl)-2-(((9H-fluoren-9-ylmethoxy)carbonyl)amino)propanoate (60.0 g, 114 mmol) described in Production Example 1-2-6 and ethyl acetate (1331 mL) was added lithium iodide (92.0 g, 685 mmol) at room temperature. The resultant mixture was stirred under reflux for 23 hours and 45 minutes. The reaction mixture was cooled to 0° C., and a precipitate was collected by filtration. To the resultant solid was added 1 N hydrochloric acid (228 mL). The resultant solution was extracted with ethyl acetate. An organic layer was dried over anhydrous magnesium sulfate and then filtrated. The solvent was evaporated under a reduced pressure to give the title compound (42.2 g, yield: 72%).

$^1$H-NMR Spectrum (400 MHz, CDCl$_3$) δ (ppm): 3.05-3.15 (1H, m), 3.18-3.30 (1H, m), 4.15-4.23 (1H, m), 4.25-4.50 (2H, m), 4.60-4.70 (1H, m), 4.99 (2H, m), 5.29 (1H, d, J=7.6 Hz), 6.64-6.73 (2H, m), 7.06 (1H, dd, J=8.0 Hz, 9.6 Hz), 7.24-7.44 (9H, m), 7.55 (2H, dd, J=6.4 Hz, 6.4 Hz), 7.76 (2H, d, J=7.6 Hz).

ESI-MS (m/z): 512.30 [M+H]$^+$.

Production Example 1-3-1

1-(1-(Diphenylmethyl)azetidin-3-yl)-4-ethylpiperazine

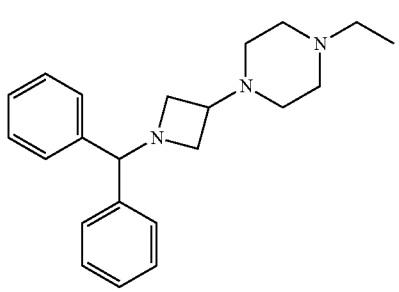 [SMILES: CCN1CCN(C2CN(C(c3ccccc3)c3ccccc3)C2)CC1]

To a mixed solution of a commercially available product of 1-(diphenylmethyl)azetidin-3-one (10.1 g, 42.6 mmol), THF (100 mL) and acetic acid (5.00 mL) was added ethylpiperazine (6.48 mL, 51.1 mmol) at room temperature. The resultant mixture was stirred at room temperature for 45 minutes. Sodium triacetoxyborohydride (18.1 g, 85.1 mmol) was added to the reaction mixture at room temperature and then stirred at room temperature for 15 hours. Sodium hydrogen carbonate and water were added to the reaction mixture, and the resultant solution was then extracted with ethyl acetate. An organic layer was washed with saturated brine, then dried over anhydrous magnesium sulfate, and then filtrated. The solvent was evaporated under a reduced pressure, and the resultant residue was purified by silica gel column chromatography (ethyl acetate-methanol) and was then further purified by NH silica gel column chromatography (heptane:ethyl acetate=2:1 and the 1:1) to give the title compound (12.7 g, yield: 89%).

$^1$H-NMR Spectrum (400 MHz, CDCl$_3$) δ (ppm): 1.07 (3H, t, J=7.6 Hz), 2.20-2.65 (10H, m), 2.85-2.93 (2H, m), 2.95-3.05 (1H, m), 3.35-3.45 (2H, m), 4.41 (1H, s), 7.15-7.20 (2H, m), 7.23-7.29 (4H, in), 7.37-7.42 (4H, m).

Production Example 1-3-2

1-(Azetidin-3-yl)-4-ethylpiperazine

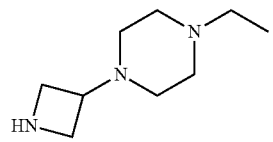

To a mixed solution of 1-(1-(diphenylmethyl)azetidin-3-yl)-4-ethylpiperazine (12.7 g, 37.9 mmol) described in Production Example 1-3-1 and methanol (50 mL) was added palladium hydroxide-carbon (5.00 g) at room temperature. The resultant mixture was stirred under a hydrogen atmosphere at room temperature and at 0.35 MPa to 0.40 MPa for 10 hours. The reaction mixture was purged with a nitrogen atmosphere and was then filtrated using Celite. A filtrate was concentrated under a reduced pressure to give the title compound in the form of a mixture (12.4 g) with benzylbenzene. The product was used in the subsequent reaction without further purification.

$^1$H-NMR Spectrum (400 MHz, CDCl$_3$) δ (ppm): 1.09 (3H, t, J=7.2 Hz), 2.10-2.80 (10H, m), 3.20-3.30 (1H, m), 3.53-3.60 (2H, m), 3.60-3.70 (2H, m).

Example 2

A crystal of (6S,9aS)-N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide.

Isopropyl acetate (1.5 mL) was added to (6S,9aS)-N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide (150 mg) described in Example 1, and stirred at 85° C. for one hour and further overnight at room temperature. The resulting suspension was collected by filtration, washed with isopropyl acetate cooled to 4° C., and then dried under reduced pressure at 45° C. to obtain 141.2 mg of a white solid. 1-Propanol (0.4 mL) was added to 100 mg of the obtained solid, and the mixture was heated and dissolved at 95° C. 1-Propanol (0.1 mL) was added, and the mixture was stirred at room temperature. Heptane (1.5 mL) was added to the resulting suspension at room temperature. The suspension was collected by filtration, washed with heptane cooled to 4° C., and then dried under reduced pressure at 45° C. to obtain 92.1 mg of the title compound.

$^1$H-NMR (600 MHz, CD$_3$OD) δ (ppm): 1.15 (t, J=7 Hz, 3H), 2.0-3.1 (br, 8H), 3.13 (dd, J=14, 7 Hz, 1H), 3.32 (m, 1H), 3.33 (m, 1H), 3.44 (dd, J=14, 5 Hz, 1H), 3.46 (d, J=17 Hz, 1H), 3.54 (dd, J=12, 4 Hz, 1H), 3.62 (dd, J=13, 6 Hz, 1H), 3.69 (dd, J=13, 7 Hz, 1H), 3.79 (dd, J=8, 5 Hz, 1H), 3.86 (dd, J=8, 6 Hz, 1H), 3.89 (t, J=11 Hz, 1H), 4.03 (t, J=8 Hz, 1H), 4.06 (t, J=8 Hz, 1H), 4.25 (d, J=15 Hz, 1H), 4.33 (d, J=16 Hz, 1H), 4.41 (d, J=16 Hz, 1H), 4.77 (d, J=16 Hz, 1H), 5.12-5.18 (m, 2H), 5.27 (dd, J=7, 5 Hz, 1H), 5.84 (m, 2H), 6.30 (d, J=8 Hz, 1H), 6.38 (m, 1H), 6.40 (m, 1H), 6.51 (d, J=8 Hz, 1H), 6.88 (dd, J=9, 8 Hz, 1H), 7.25 (dd, J=8, 7 Hz, 1H), 7.28 (d, J=8 Hz, 2H), 7.34 (dd, J=8, 7 Hz, 2H), 7.47 (dd, J=8, 8 Hz, 1H)

Test Example 1: Detection of Wnt Signal pcDNA3.1(+) (invitrogen) was cleaved with restriction enzymes BglII and NotI, and an adapter BEHKS having a sequence shown below (containing restriction enzyme sites BglII, EcoRI, HindIII, KpnI, SacI and NotI) was inserted thereinto, thereby producing a plasmid pNeo-HKS.

```
BEHKS-F
                                          (SEQ ID NO: 1)
5'-gatctgaattcaggcttctcgagggtacctctagagagctcgc-3'

BEHKS-R
                                          (SEQ ID NO: 2)
5'-ggccgcgagctctctagaggtaccctcgagaagcttgaattca-3'
```

Subsequently, a fragment having a length of about 2700 bp (containing a Wnt-responsive sequence and a luciferase gene), which was prepared by cleaving from a TOPglow plasmid contained in a TOPglow/FOPglow TCF Reporter Kit (upstate Catalog#17-366) with restriction enzymes HindIII and KpnI, was inserted between HindIII and KpnI in pNeo-HKS, thereby producing a plasmid pNeo-TOP. The plasmid pNeo-TOP was introduced into human fetus-derived renal cell strain HEK293, then a compound was selected using G418, and then a cell clone strain was established by a limiting dilution method. The cell clone strain was subjected to a Wnt signal detection test.

The cell clone strain was subcultured in a D-MEM glucose-rich culture medium (Wako Pure Chemical Industries, Ltd.) containing 10% FBS, and cells in a growth phase were used in the test. Cells were collected using trypsin-EDTA, the number of the cells was counted, and then the cells were suspended in a D-MEM glucose-rich culture medium containing 10% FBS so that the number of cells became 2×10$^5$ cells/mL. The cell suspension was added to a 96-well cell culture plate (Greiner Bio-One Co., Ltd., product number: 655083) in an amount of 0.1 mL/well and then cultured overnight in a 5% CO$_2$ incubator (37° C.). After the culturing, a substance to be tested, which was dissolved in DMSO, was diluted with a D-MEM glucose-rich culture medium containing 10% of FBS and 80 mM of LiCl to produce a sample solution. The sample solution (0.1 mL) was added to each well and then cultured in a 5% CO$_2$ incubator (37° C.) overnight. Six hours after the addition of the sample solution, a supernatant was removed from each well, and then 50 µL of Bright-Glo™ Luciferase substrate (Promega, product number: E2620) was added thereto. The plate was put on a plate mixer for several seconds, and then the emission of light from each well was measured using a EnVision™ Multilabel plate reader (PerkinElmer Co., Ltd.). The Wnt signal activation rate (%) of each well was determined, and a concentration (IC$_{50}$) which is required for inhibiting the Wnt signal activity of a substance of interest by 50% was calculated, wherein the luminosity of a well to which a sample solution was not added and LiCl was added was defined as a 100% Wnt signal activity and the luminosity of a well to which either of a sample solution or LiCl was not added was defined as a 0% Wnt signal activity. IC$_{50}$ of the compound of Example 1 was 0.06 µM.

Test Example 2: Effect of Regressing Small Intestinal Polyps in APC$^{Min/+}$ Mouse An APC gene (an adenomatous polyposis coli gene), a Wnt signal degradation regulation factor, is called "colorectal cancer suppressor gene" and is a causal gene of familial adenomatous polyposis. If a mutation occurs in the APC gene, a colorectal mucosal cell begins to proliferate disorderly to form colorectal polyps that can be called a precancerous lesion. Thus, it is known that the gene has an important role in the initial stage of a process of onset of colorectal cancer.

In a mouse in which the APC gene is mutated (a APC$^{Min/+}$ mouse), many polyps are developed in the intestinal tract like a familial adenomatous polyposis patient. Therefore, the mouse is useful for the clarification of the mechanism of the onset or invasion of cancer based on a WNT signal, and is a standard model that has been used for the studies on the prevention, diagnosis and treatment of colorectal cancer.

APC$^{Min/+}$ mice (C57BL/6J-APC<Min>/J Hetero, female, Sunplanet Co., Ltd.) were grouped so that the average of the body weights of mice in a group became almost the same as one another at the first day of the administration. An analyte was prepared by being dissolved a test substance (Example compound) in 0.1 N HCl so that the concentration became a desired administration concentration, and then stored in a refrigerator at 4° C. To a control (vehicle) group, an administration solvent was administered orally under the same conditions as a test material. The analyte was continuously administered through an oral route at dosages of 50 mg/kg and 75 mg/kg two times daily for 4 days, and the following three days were provided as drug holidays. This procedure was defined as one cycle, and the administration was performed for 16 days in total (i.e., 4 days×4 cycles). The experiment was carried out on 6 to 7 mice per group. With respect to each of the control group and the test substance-administered group, the value of the body weight on the final day to the body weight on the first day (i.e., a relative body weight: RBW) was calculated. A test substance-administered group of which the (RBW of the test substance-administered group)/(RBW of the control group) was 0.8 or more was determined as a group that could be administered safely. With respect to the test substance-administered group, the actual number of polyps after the administration of the test substance and the standard error of the actual number compared with the number of polyps in the control on the final day (i.e., the 25th day counted from the first day of the administration) are shown in FIG. 1. In this test, polyps formed in the small intestine and the colon were counted. A statistical analysis (Dunnett's test) of the test substance-administered group relative to the control group was carried out, and a P value was reported.

Test Example 3: Anti-Tumor Effect in Human K562 Subcutaneous Transplantation Model A preparation of a human chronic myologenous leukemia cell strain K562 (which had been cultured in a RPMI-1640 liquid culture medium supplemented with 10% FBS and penicillin/streptomycin) which was so prepared with PBS (Wako Pure Chemical Industries, Ltd.; Cat#045-29795) that the density became $2 \times 10^8$ cells/mL was mixed with MATRI-GEL (BD Biosicence, Cat#: 354234) at a mixing ratio of 1:1, thereby preparing a cell suspension having a density of $1 \times 10^8$ cells/mL. The resulting cell suspension was transplanted subcutaneously into the right flank of each of six-week-old nude mice (CAnN.Cg-Foxn1nu/CrlCrlj, female, Charles River Laboratories Japan) at a dose of 100 µL. Seven days after the transplantation, the shorter diameter and the longer diameter of a tumor were measured using an electronic digital caliper (Digimatic™ Caliper, Mitutoyo Corporation) to calculate the tumor volume in accordance with the following equation.

Tumor volume (mm³)=(longer diameter (mm))× (shorter diameter (mm))×(shorter diameter (mm))/2

Figure 2:
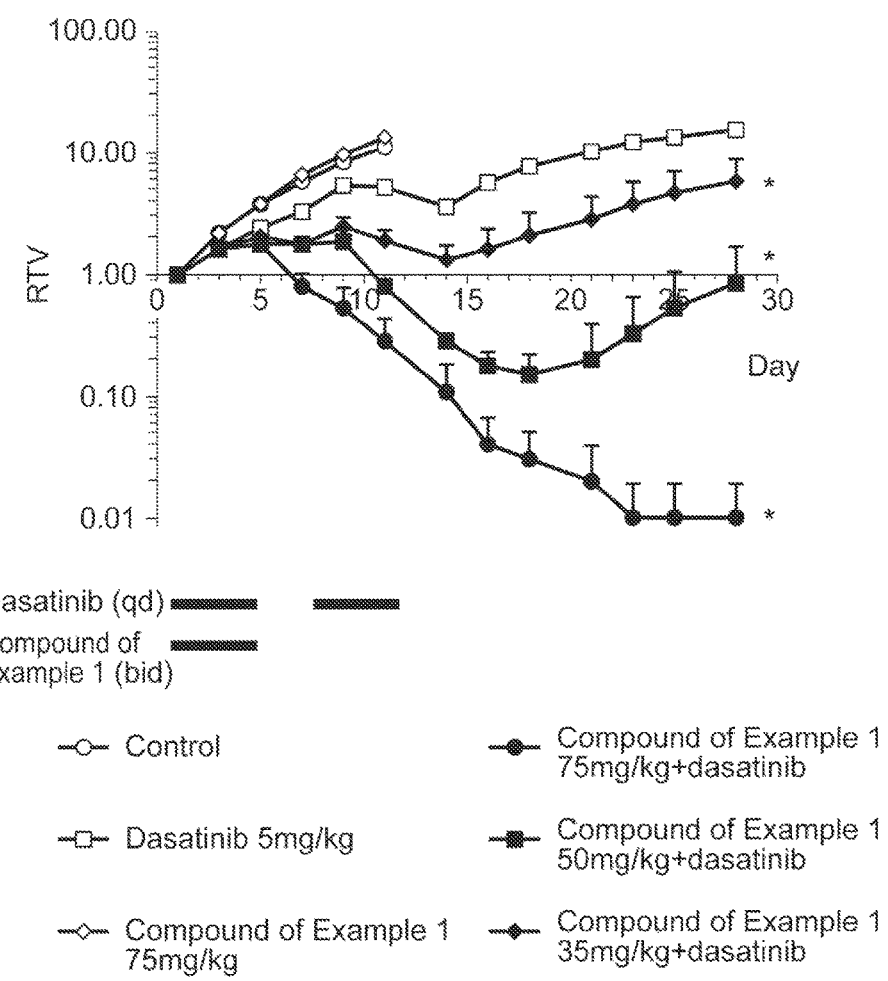
FIG. 2 shows the results of Test Example 3. The abscissa indicates the number of days elapsed, and the ordinate indicates the relative tumor volume (RTV) with respect to the tumor volume on day 0.
Figure 3:
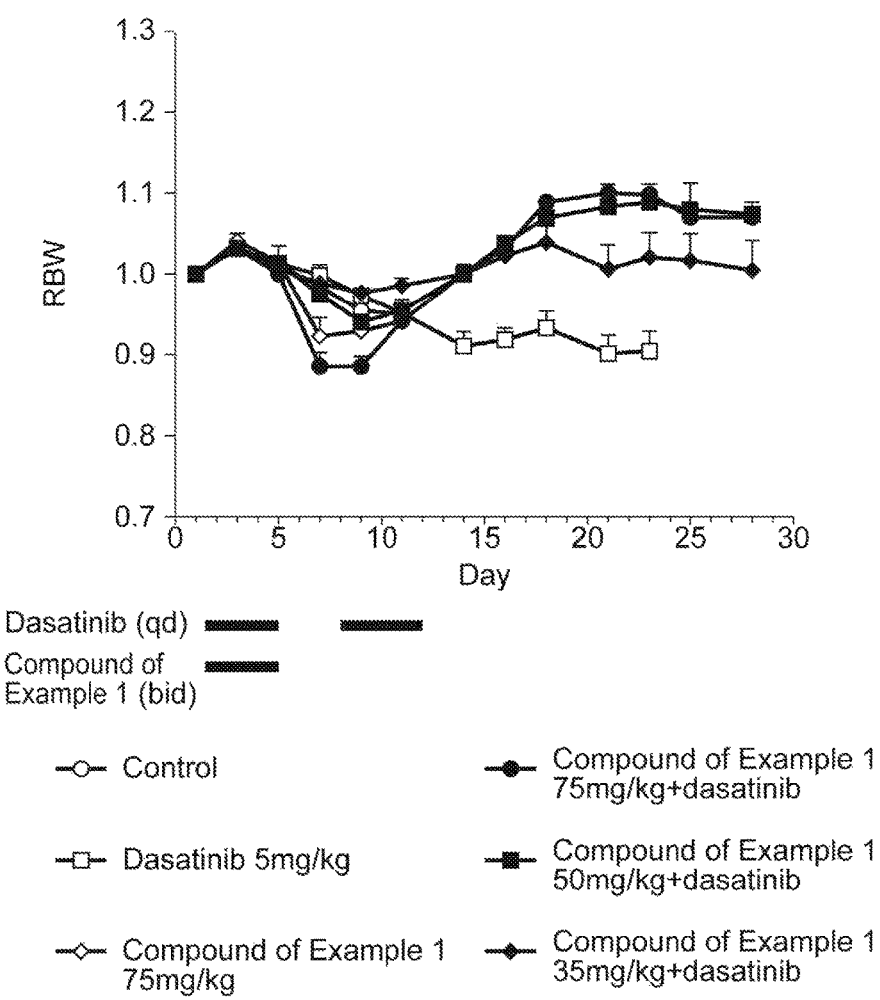
FIG. 3 shows the results of Test Example 3. The abscissa indicates the number of days elapsed, and the ordinate indicates the relative body weight (RBW) with respect to the body weight on day 0.

The mice were grouped in such a manner that the average value of the tumor volumes in mice in a group, which were determined on the basis of the tumor volume on the first day of the administration. An analyte was prepared by being dissolved a compound of Example 1 in 0.1 N HCl so that the dose amount became 10 mL/kg. A Dasatinib administration solution was prepared by dissolving Dasatinib, Free Base (LC Laboratories, Cat. No: D-3307) in a 1:1 solution of Otsuka distilled water (Otsuka Pharmaceutical Co., Ltd., Cat#: 1324) and PROPYLENE GLYCOL (Wako Pure Chemical Industries, Ltd., Cat#: 164-04996) so that the dosage amount became 10 mL/kg. An analyte was administered orally continuously for 5 days starting from the first day of the administration in two divided doses daily (bid). A Dasatinib administration solution was administered orally once daily (qd) for 5 days continuously, and the following two-day drug holidays was set. This procedure was defined as one cycle, and the administration was performed in two cycles in total. A control group was a group to which any example compound was not administered. In the experiment, one group includes 9 to 10 mice. With respect to the control group, a group to which only an Example compound was administered, a group to which only Dasatinib was administered, and an a group to which both an Example compound and Dasatinib were administered (hereinafter referred as 'combined administered group'), the tumor volumes and body weights were measured over time for a period from the first day to the 28th day. With respect to the control group and the group to which only the Example compound was administered, the measurement was carried out for a period from the first day to the 11th day. In every measurement, a tumor volume (a relative tumor volume: RTV) and a body weight (a relative body weight: RBW) were calculated relative to the values for the first day, and graphs determined for a period from the first day of the administration to the 28th day are shown in FIGS. 2 and 3. Further, a statistic analysis (Dunnett's test) was carried out on the group to which both the Example compound and Dasatinib were administered compared with the group to which only Dasatinib was administered using a RTV value on day 28, and a group of which the P value was 0.05 or less was marked with an asterisk (*). Further, the number of individuals in which a tumor was not observed by visual judgment and was impalpable (i.e., having a non-palpable tumor) on day 28 are also shown in Table 6. At this time, a statistic analysis (Fisher's test) was carried out on the group to which both the Example compound and Dasatinib were administered compared with the group to which only Dasatinib was administered, and a group of which P value was 0.05 or less was marked with an asterisk (*) and a group in which P value is 0.01 or less was marked with asterisks (***).

TABLE 1

| Administered compound | the number of individuals in which a tumor was not observed by visual judgment/total number of administered individuals |
|---|---|
| Vehicle | 0/10 |
| Dasatinib 5 mg/kg | 0/9 |
| Dasatinib 5 mg/kg + Compound of Example 1 35 mg/kg | 6/10* |
| Dasatinib 5 mg/kg + Compound of Example 1 50 mg/kg | 9/10*** |
| Dasatinib 5 mg/kg + Compound of Example 1 75 mg/kg | 10/10*** |

Test Example 4: Powder X-Ray Diffraction

Figure 4:
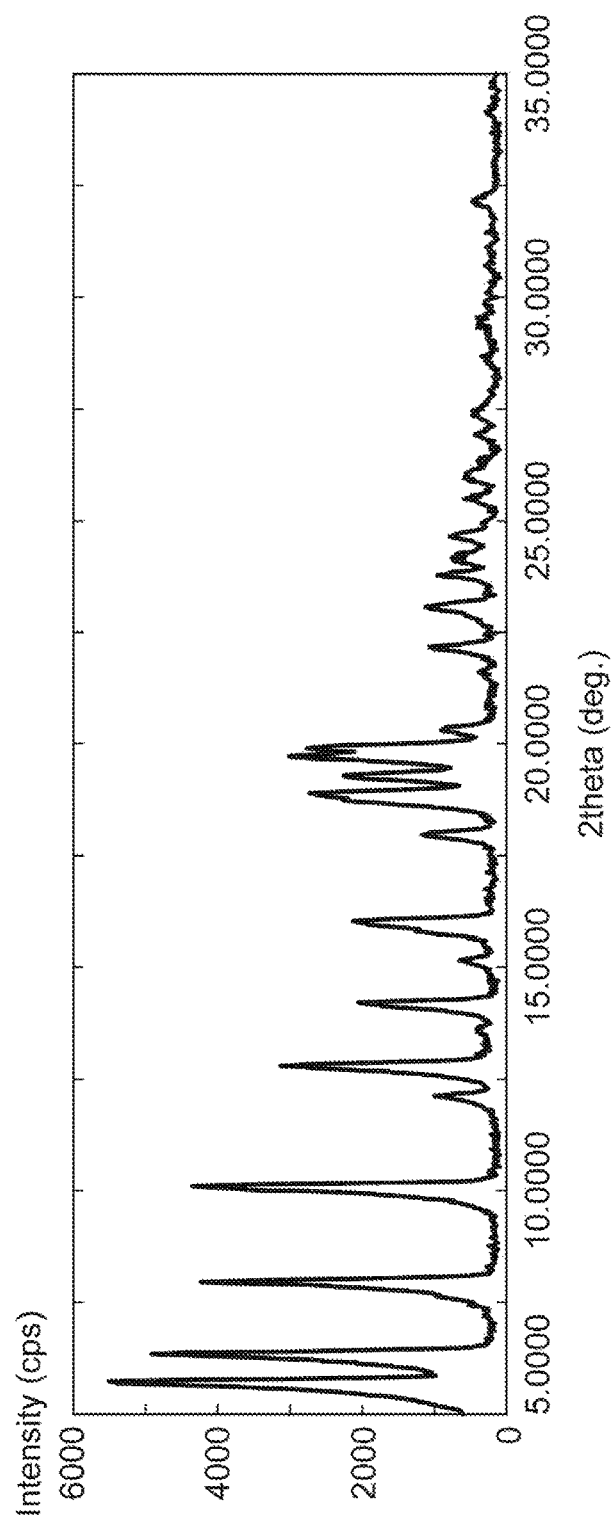
FIG. 4 is a powder X-ray diffraction pattern of the crystal of Compound 1 in Test Example 4. The abscissa indicates the diffraction angle (2θ), and the ordinate indicates the peak intensity.
Figure 5:
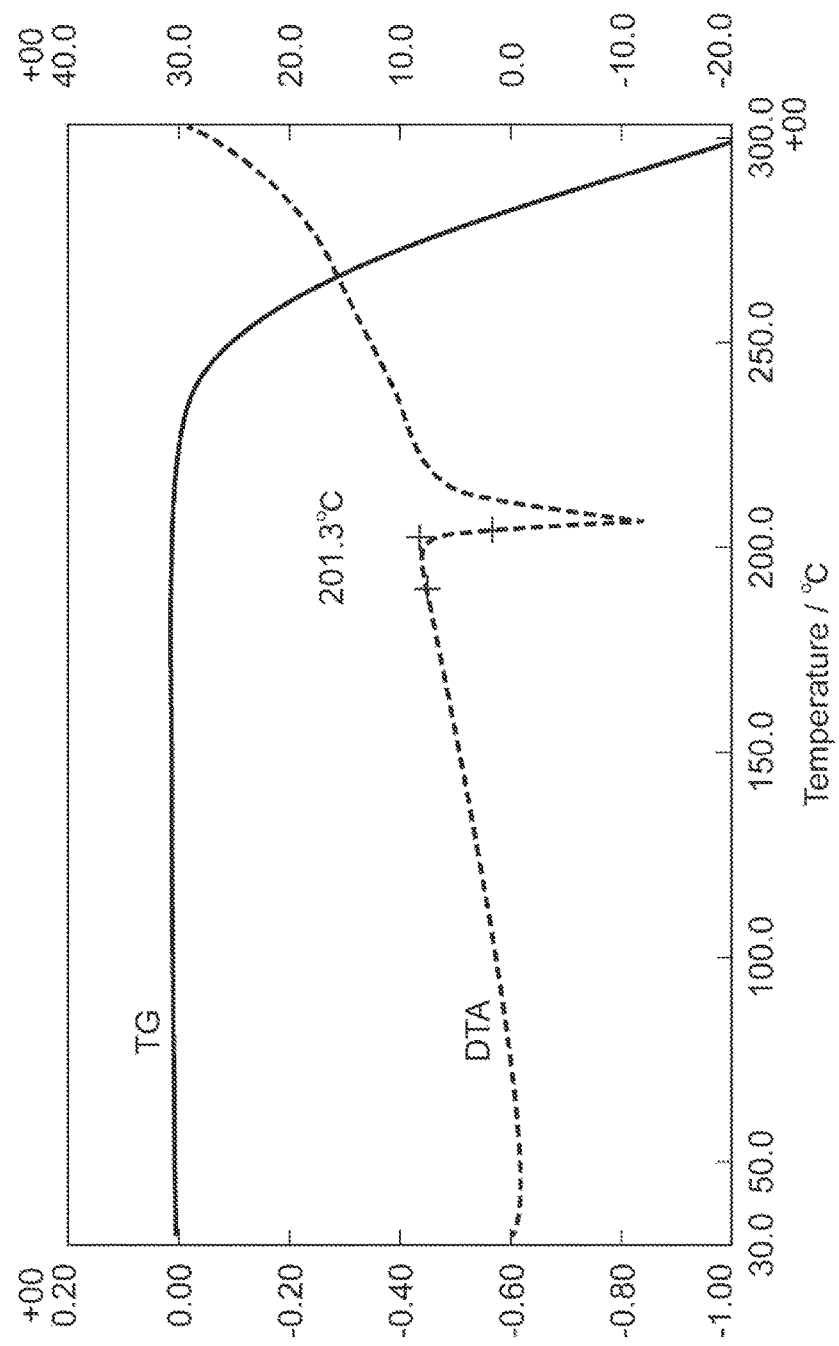
FIG. 5 shows the results of Test Example 5. The abscissa indicates the temperature, the left ordinate indicates the weight change in thermogravimetry (TG), and the right ordinate indicates the heat flow in differential thermal analysis (DTA).

The crystal of Compound 1 obtained in Example 2 was placed on the sample stage of a powder X-ray diffraction apparatus and analyzed under the following conditions. The results are shown in FIG. 4.
(Measurement Conditions)
  Target: copper
  Detector: scintillation counter
  Tube voltage: 50 kV
  Tube current: 300 mA
  Slit: divergent slit: 0.5 mm; scattering slit: open; light-receiving slit: open
  Scan rate: 5°/minute
  Sampling interval: 0.02°
  Scan range: 5° to 35°
  Sample holder: aluminum holder Test Example 5: Thermal Analysis The crystal obtained in Example 2 was accurately weighed into an aluminum sample pan and subjected to thermogravimetry (TG) and differential thermal analysis (DTA) under the following conditions.
The results are shown in FIG. 5.
(Measurement Conditions)
Atmosphere: under 40 mL/minute of nitrogen gas flow
Reference: empty aluminum sample pan
Heating rate: 10° C./minute
Sampling interval: 1 second
Measurement temperature range: 40 to 300° C.

Test Example 6: Solid State $^{13}$C NMR Spectrum

The solid state $^{13}$C NMR spectrum was measured under the following conditions. The results are shown in FIG. 6.
(Measurement Conditions)
Used apparatus: Avance400 MHz (manufactured by BRUKER) 7
mm-CPMAS probe (manufactured by BRUKER)
Measured nucleus: $^{13}$C (resonant frequency 100.6248425 MHz)
Measurement temperature: room temperature (22° C.)
Pulse mode: CPTOSS measurement
Rotation number: 5,000 Hz
Pulse repetition time: 4 second
Contact time: 1 millisecond
Number of scans: 8,000
Reference material: glycine (external reference: 176.03 ppm)

The solid state $^{13}$C NMR spectrum was obtained by CPTOSS method (a method for eliminating spinning side bands) with carbon nucleus (resonance frequency 100.6 MHz) using an NMR instrument, BRUKER Avance 400 MHz equipped with a 7 mm CPMAS probe (manufactured by BRUKER). The sample tube enclosing approximately 300 mg of a solid sample was rotated at 5 kHz and measured using contact time of 1 millisecond, pulse delay time of 4 second and number of scans of 8000 at room temperature (22° C.). Chemical shifts were corrected by an external reference method with carbonyl carbon of glycine being 176.03 ppm.

2H-pyrazino[2,1-c][1,2,4]triazine-1(6H)-carboxamide, wherein the crystal comprises diffraction peaks at the diffraction angles (2θ±0.2°) of 5.8°, 6.4° and 10.1° in powder X-ray diffraction.

2. The crystal according to claim 1, wherein the crystal further comprises diffraction peaks at the diffraction angles (2θ±0.2°) of 8.0° and 12.8° in powder X-ray diffraction.

3. The crystal according to claim 2, wherein the crystal further comprises diffraction peaks at the diffraction angles (2θ±0.2°) of 14.2°, 16.0°, 18.9°, 19.7° and 23.1° in powder X-ray diffraction.

4. A crystal of (6S,9aS)-N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide, wherein the crystal comprises peaks at the chemical shifts (δ±0.5 ppm) of 141.1 ppm and 158.1 ppm in $^{13}$C solid state NMR spectrum.

5. The crystal according to claim 4, wherein the crystal further comprises peaks at the chemical shifts (δ±0.5 ppm) of 134.0 ppm and 165.1 ppm in $^{13}$C solid state NMR spectrum.

6. The crystal according to claim 5, wherein the crystal further comprises peaks at the chemical shifts (δ±0.5 ppm) of 12.6 ppm, 55.5 ppm and 118.5 ppm in $^{13}$C solid state NMR spectrum.

7. A pharmaceutical composition comprising an effective amount of the crystal according to claim 1 and a pharmaceutically acceptable additive.

---

---

The invention claimed is:

1. A crystal of (6S,9aS)-N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro- 8. A pharmaceutical composition comprising an effective amount of the crystal according to claim 4 and a pharmaceutically acceptable additive.

* * * * *

SEQUENCE LISTING

```
<160> NUMBER OF SEQ ID NOS: 2

<210> SEQ ID NO 1
<211> LENGTH: 43
<212> TYPE: DNA
<213> ORGANISM: Artificial Sequence
<220> FEATURE:
<223> OTHER INFORMATION: BEHKS-F

<400> SEQUENCE: 1
gatctgaatt caagcttctc gagggtacct ctagagagct cgc         43

<210> SEQ ID NO 2
<211> LENGTH: 43
<212> TYPE: DNA
<213> ORGANISM: Artificial Sequence
<220> FEATURE:
<223> OTHER INFORMATION: BEHKS-R

<400> SEQUENCE: 2
ggccgcgagc tctctagagg taccctcgag aagcttgaat tca         43
```